United States Patent [19]

Martin et al.

[11] Patent Number: 5,741,778

[45] Date of Patent: Apr. 21, 1998

[54] METHOD FOR TREATING HUNTINGTON'S DISEASE USING GLIAL CELL LINE-DERIVED NEUROTROPHIC FACTOR (GDNF) PROTEIN PRODUCT

[75] Inventors: David Martin, Boulder; Gerald D. Miller, Nederland, both of Colo.

[73] Assignee: Amgen Inc., Thousand Oaks, Calif.

[21] Appl. No.: 618,543

[22] Filed: Mar. 19, 1996

[51] Int. Cl.$^6$ .............. A61K 47/00; A61K 31/685; A61F 2/00

[52] U.S. Cl. .............. 514/12; 424/85.1; 435/69.1; 435/69.4

[58] Field of Search .............. 514/12; 424/85.1; 435/69.1, 69.4

[56] References Cited

U.S. PATENT DOCUMENTS

| | | | |
|---|---|---|---|
| 4,518,584 | 5/1985 | Mark et al. | 424/85.2 |
| 4,892,538 | 1/1990 | Aebischer et al. | 604/891.1 |
| 5,011,472 | 4/1991 | Aebischer et al. | 604/50 |
| 5,106,627 | 4/1992 | Aebischer et al. | 424/424 |
| 5,252,714 | 10/1993 | Harris et al. | 530/391.9 |
| 5,272,071 | 12/1993 | Chappel | 435/172.3 |

FOREIGN PATENT DOCUMENTS

| | | |
|---|---|---|
| 401384 | 12/1990 | European Pat. Off. . |
| 423 980 | 4/1991 | European Pat. Off. . |
| 154 316 | 9/1995 | European Pat. Off. . |
| WO 92/16221 | 10/1992 | WIPO . |
| WO 93/06116 | 4/1993 | WIPO . |
| 9526408 | 9/1995 | WIPO . |

OTHER PUBLICATIONS

Arenas et al. (1995), 'GDNF Prevents Degeneration and Promotes the Phenotype of Brain Noradrenergic Neurons In Vivo', Neuron 15:1465–1473.

Beal et al. (1991), 'Chronic Quinolinic Acid Lesions in Rats Closely Resemble Huntington'Disease', J. Neurosci 11(6):1649–1659.

Choi (1988), 'Glutamate Neurotoxicity and Diseases of the Nervous System', Neuron 1:623–634.

Greenamyre et al. (1985), 'Alterations in L–Glutamate Binding in Alzheimer'and Huntington's Diseases', Science 227:1496–1499.

Humpel et al. (1994), 'Neurons of the Hippocampal Formation Express Glial Cell Line–Derived Neurotrophic Factor Messenger RNA in Response to Kainate–Induced Excitation', Neurosci. 59(4):791–795.

Lin et al. (1993), 'GDNF: A Glial Cell Line–Derived Neurotrophic Factor for Midbrain Dopaminergic Neurons', Science 260:1130–1132.

Martin et al. (1987), 'Biphasic effect of quinolinate on frog spinal, but not rat cortical, neurones: N–methyl–D–aspartate–like depolarisation and a novel type of hyperpolarisation', Neurosci. Lett.. 75:175–180.

Martin et al. (1994), rhGDNF Prevents Kainic Acid Induced Seizures and the Associated Neuronal Cell Death, Soc. Neurosci. Abstr. 20:193.12.

Martin et al. (1995), 'Potent inhibitory effects of glial derived neurotrophic factor against kainic acid mediated seizures in the rat', Brain Res. 683:172–178.

Norman et al. (1991), 'Differential Loss of Neurochemical Markers following Quinolinic Acid–Induced Lesions of Rat Striatum', Exp. Neurology 114:132–135.

Perez–Navarro et al. (1994), Nerve Growth Factor and Basic Fibroblast Growth Factor Protect Cholinergic Neurons Against Quinolinic Acid Excitotoxicity in Rat Neostriatum, Eur. J. Neurosci. 6:706–711.

Portera–Cailliau et al. (1995), 'Evidence for Apoptotic Cell Death in Huntington Disease and Excitotoxic Animal Models', J. of Neuroscience 15(5):3775–3787.

Roberts et al. (1993), 'Intrastriatal Injections of Quinolinic Acid or Kainic Acid: Differential Patterns of Cell Survival and the Effects of Data Analysis on Outcome', Exp. Neurol. 124:274–282.

Schwarcz et al. (1991), 'Quinolinic Acid and Kynurenic Acid in the Mammalian Brain', Kynurenine and Serotonin Pathways (Plenum Press, New York) pp. 185–199.

Susel et al. (1991), 'Prolonged infusion of quinolinic acid into rat striatum as an excitotoxic model of neurodegenerative disease', Neuroscience Lett. 121:234–238.

Ho et al. Neuroreport, 6(10), pp. 1454–1458 (1995) (Abstract).

Lin et al., Science, vol. 260:1130–32 (1993).

Greenamyre et al., Science, vol. 227, pp. 1496–1499 (1985).

*Primary Examiner*—Cecilia J. Tsang
*Assistant Examiner*—P. Lynn Touzeeau
*Attorney, Agent, or Firm*—Daniel R. Curry; Ron K. Levy; Steven M. Odre

[57] ABSTRACT

Methods are provided for preventing or reducing N-methyl-D-aspartate (NMDA) receptor agonist-mediated neuronal cell death by administering a glial cell line-derived neurotrophic factor (GDNF) protein product.

11 Claims, 4 Drawing Sheets

FIG.4

```
TCA CCA GAT AAA CAA ATG GCA GTG CTT CCT AGA AGA GAG CGG AAT
Ser Pro Asp Lys Gln Met Ala Val Leu Pro Arg Arg Glu Arg Asn
             5                  10                      15

CGG CAG GCT GCA GCT GCC AAC CCA GAG AAT TCC AGA GGA AAA GGT
Arg Gln Ala Ala Ala Ala Asn Pro Glu Asn Ser Arg Gly Lys Gly
            20                  25                      30

CGG AGA GGC CAG AGG GGC AAA AAC CGG GGT TGT GTC TTA ACT GCA
Arg Arg Gly Gln Arg Gly Lys Asn Arg Gly Cys Val Leu Thr Ala
            35                  40                      45

ATA CAT TTA AAT GTC ACT GAC TTG GGT CTG GGC TAT GAA ACC AAG
Ile His Leu Asn Val Thr Asp Leu Gly Leu Gly Tyr Glu Thr Lys
            50                  55                      60

GAG GAA CTG ATT TTT AGG TAC TGC AGC GGC TCT TGC GAT GCA GCT
Glu Glu Leu Ile Phe Arg Tyr Cys Ser Gly Ser Cys Asp Ala Ala
            65                  70                      75

GAG ACA ACG TAC GAC AAA ATA TTG AAA AAC TTA TCC AGA AAT AGA
Glu Thr Thr Tyr Asp Lys Ile Leu Lys Asn Leu Ser Arg Asn Arg
            80                  85                      90

AGG CTG GTG AGT GAC AAA GTA GGG CAG GCA TGT TGC AGA CCC ATC
Arg Leu Val Ser Asp Lys Val Gly Gln Ala Cys Cys Arg Pro Ile
            95                  100                     105

GCC TTT GAT GAT GAC CTG TCG TTT TTA GAT GAT AAC CTG GTT TAC
Ala Phe Asp Asp Asp Leu Ser Phe Leu Asp Asp Asn Leu Val Tyr
            110                 115                     120

CAT ATT CTA AGA AAG CAT TCC GCT AAA AGG TGT GGA TGT ATC
His Ile Leu Arg Lys His Ser Ala Lys Arg Cys Gly Cys Ile
            125                 130
```

METHOD FOR TREATING HUNTINGTON'S DISEASE USING GLIAL CELL LINE-DERIVED NEUROTROPHIC FACTOR (GDNF) PROTEIN PRODUCT

BACKGROUND OF THE INVENTION

1. Field of the Invention

The present invention relates generally to methods for treating neurodegenerative diseases that are associated with N-methyl-D-aspartate (NMDA) receptor agonist-mediated cell death by administering a therapeutically effective amount of glial cell line-derived neurotrophic factor (GDNF) protein product. In particular, the present invention relates to the treatment of neurodegenerative diseases such as Huntington's disease.

2. Background

Neurotrophic factors are natural proteins, found in the nervous system or in non-nerve tissues innervated by the nervous system, that function to promote the survival and maintain the phenotypic differentiation of nerve and/or glial cells (Varon et al., *Ann. Rev. Neuroscience*, 1:327, 1979; Thoenen et al., *Science*, 229:238, 1985). Neurotrophic factors have been found useful in treating the degeneration of nerve cells and loss of differentiated function that results from nerve damage. Nerve damage is caused by conditions that compromise the survival and/or proper function of one or more types of nerve cells, including: (1) physical injury, which causes the degeneration of the axonal processes and/or nerve cell bodies near the site of injury, (2) temporary or permanent cessation of blood flow (ischemia) to parts of the nervous system, as in stroke, (3) intentional or accidental exposure to neurotoxins, such as the cancer and AIDS chemotherapeutic agents cisplatinum and dideoxycytidine (ddC), respectively, (4) chronic metabolic diseases, such as diabetes or renal dysfunction, or (5) neurodegenerative diseases such as Parkinson's disease, Alzheimer's disease, and Amyotrophic Lateral Sclerosis (ALS), which result from the degeneration of specific neuronal populations. In order for a particular neurotrophic factor to be potentially useful in treating nerve damage, the class or classes of damaged nerve cells must be responsive to the factor; different neurotrophic factors typically affect distinctly different classes of nerve cells.

The first neurotrophic factor to be identified was nerve growth factor (NGF). NGF is the first member of a defined family of trophic factors, called the neurotrophins, that currently includes brain-derived neurotrophic factor (BDNF), neurotrophin-3 (NT-3), NT-4/5, and NT-6 (Thoenen, *Trends. Neurosci.*, 14:165–170, 1991; Lapchak et al., *Rev. Neurosci.*, 3:1–10, 1993; Bothwell, *Ann. Rev. Neurosci.*, 18:223–253, 1995). These neurotrophins are known to act via the family of trk tyrosine kinase receptors, i.e., trkA, trkB, trkC, and the low affinity p75 receptor (Lapchak et al., *Rev. Neurosci.*, 3:1–10, 1993; Bothwell, *Ann. Rev. Neurosci.*, 18:223–253, 1995; Chao et al., *TINS* 18:321–326, 1995).

Glial cell line-derived neurotrophic factor (GDNF) is a recently discovered protein identified and purified using assays based upon its efficacy in promoting the survival and stimulating the transmitter phenotype of mesencephalic dopaminergic neurons in vitro (Lin et al., *Science*, 260:1130–1132, 1993). GDNF is a glycosylated disulfide-bonded homodimer that has its closest structural homology to the transforming growth factor-beta (TGF-β) family of neurotrophic proteins (Lin et al., *Science*, 260:1130–1132, 1993; Krieglstein et al., *EMBO J.*, 14:736–742, 1995; Poulsen et al., *Neuron*, 13:1245–1252, 1994). In vivo, treatment with exogenous GDNF stimulates the dopaminergic phenotype of substantia nigra neurons, and restores functional deficits induced by axotomy or dopaminergic neurotoxins in animal models of Parkinson's disease (Hudson et al., *Brain Res. Bull.*, 36:425–432, 1995; Beck et al., *Nature*, 373:339–341, 1995; Tomac et al., *Nature*, 373:335–339, 1995; Hoffer et al., *Neurosci. Lett.*, 182:107–111, 1994). GDNF also has neurotrophic efficacy on brain stem and spinal cord cholinergic motor neurons, both in vivo and in vitro (Oppenheim et al., *Nature*, 373:344–346, 1995; Zurn et al., *Neuroreport*, 6:113–118, 1994; Yan et al., *Nature*, 373:341–344, 1995; Henderson et al., *Science*, 266:1062–1064, 1994). Evidence is beginning to emerge indicating that GDNF may have a larger spectrum of neurotrophic targets besides mesencephalic dopaminergic and somatic motor neurons (Yan and Matheson, *Nature*, 373:341–344, 1995; Miller et al., *Soc. Neurosci. Abstr.*, 20:1300, 1994). GDNF mRNA has been detected in muscle and Schwann cells in the peripheral nervous system and in type I astrocytes (Schaar et al., *Exp. Neurol.*, 124:368–371, 1993) in the central nervous system.

Huntington's disease (HD) is an inherited neurodegenerative disease that is characterized by involuntary chorea, dementia, emotional disturbance, and death at fifteen to twenty years after onset. It is an autosomal dominant inherited disease that affects men and women with an equal frequency of about 5 per 100,000 people. Each child of an affected parent has a 50% chance of inheriting the disease. The onset of the disease typically occurs in the fourth to fifth decade of life, after most individuals have married and had children.

The first signs of the disease are subtle: absentmindedness, irritability, and depression, accompanied by fidgeting, clumsiness, or sudden falls. Uncontrolled choreiform movements, a prominent feature of the disease, gradually increase until the patient is confined to bed or to a wheelchair. The patient's speech becomes slurred at first, then incomprehensible, and finally stops altogether. The cognitive functions also deteriorate, and eventually the ability to reason disappears. No treatment is available. Once the disease has begun its inexorable course, the patient faces years of gradually decreasing capacity, followed by total disability and certain death.

The major site of pathology in HD is the striatum, where up to 90% of the neurons may be depleted. Within the striatum there is a selective loss of certain neuronal populations. Striatal medium-sized spiny neurons, which contain the neurochemical markers gamma-aminobutyric acid (GABA), substance P, dynorphin, and enkephalin are preferentially affected. In contrast, medium-sized aspiny neurons containing the neuropeptides somatostatin and neuropeptide Y, and large aspiny neurons containing choline acetyltransferase (ChAT) activity, are spared (despite an overall loss of ChAT activity). Dopaminergic and serotonergic afferent projections are also spared. (Beal et al., *J. Neurosci.*, 11:1649–1659, 1991).

The impaired cognitive functions and eventual dementia may be due either to the loss of cortical neurons or to the disruption of normal activity in the cognitive portions of the basal ganglia, namely the dorsolateral prefrontal and lateral orbitofrontal circuits. The characteristic chorea is believed to be caused by the neuronal loss in the striatum, although a reduction in subthalamic nucleus activity may also contribute. Normally a balance is maintained among the activities of three biochemically distinct but functionally interrelated systems: (1) the nigrostriatal dopaminergic system; (2)

the intrastriatal cholinergic neurons; and (3) the GABA-ergic system, which projects from the striatum to the globus pallidus and substantia nigra. An imbalance anywhere in the dopamine, acetylcholine, or GABA systems can cause involuntary movements. Both choline acetyltransferase, the enzyme required for the formulation of acetylcholine, and glutamic acid decarboxylase, the enzyme required to synthesize GABA, are markedly decreased in the striatum of patients with HD. These enzyme deficits are consistent with the clinical observation that choreic movements worsen in patients with HD following administration of L-DOPA.

Glutamate-induced neuronal cell death is believed to contribute to Huntington's disease. Glutamate is the principal excitatory transmitter in the brain. It excites virtually all central neurons and is present in the nerve terminals in extremely high concentrations ($10^{-3}$M). Glutamate receptors are divided into four types (named after their model agonists): kainate receptors, N-methyl-D-aspartate (NMDA) receptors, a-amino-3-hydroxy-5-methyl-4-isoxazolepropionate (AMPA) receptors, and metabolotrophic receptors. Many normal synaptic transmission events involve glutamate release.

Glutamate can also induce neurotoxicity and neuronal death at high levels (Choi, D. W, *Neuron*, 1:623–634, 1988). The mechanism of cell death occurs primarily by the persistent action of glutamate on the N-methyl-D-aspartate (NMDA) type of glutamate receptors and the resulting excessive influx of $Ca^{2+}$. The excessive $Ca^{2+}$ mobilizes active $Ca^{2+}$-dependent proteases and activates phospholipase $A_2$, which in turn liberates arachidonic acid, leading to the production of substances causing inflammation and free radicals that can trigger further destructive events. These toxic changes produced by glutamate, called glutamate excitotoxicity, are believed to be the cause of cell damage and death after acute brain injury such as stroke or excessive convulsions. It has been suggested that excitotoxicity may be involved in brain ischemia, Alzheimer's disease and HD (Greenamyre et al., *Science*, 227:1496–1499, 1985; Choi, D. W, *Neuron*, 1:623–634, 1988).

Injection of glutamate receptor agonists into rat striatum can produce a pattern of neuronal cell loss similar to HD. Although the majority of the neurons within the actual injection site die, there is a surrounding gradual transition zone that exhibits selective cell death. Initial studies with kainic acid (KA)-induced lesions showed a striking resemblance to HD. KA is isolated from the seaweed *Diginea simplex* and is not found in the mammalian brain. Intrastriatal injections of KA result in neuronal loss and gliosis, with reductions in markers of intrinsic striatal neurons, yet a preservation of dopaminergic afferents. These KA-induced lesions, however, are an imperfect model of HD because they result in a significant depletion of somatostatin levels and a loss of somatostatin neurons. Lesions produced by NMDA receptor agonists such as quinolinic acid (QA) provide a better model of HD, because they result in relative sparing of somatostatin and neuropeptide Y levels, despite significant depletions of both GABA and substance P levels. Long-term (6 months to 1 year) follow-up of QA lesions reveals increases in somatostatin and neuropeptide Y and in serotonin and HIAA (results not found after long-term follow-up of KA lesions), which are similar to the findings in actual HD patients. Chronic QA lesions therefore closely resemble the neurochemical features of HD. (Beal et al., *J. Neurosci.*, 11:1649–1659, 1991.) Others have confirmed that QA-induced injury of the striatum can resemble the histopathology of HD (See, e.g., Roberts et al., *Exp. Neurol.*, 124:274–282, 1993).

Of general interest to the present invention is WO93/06116 (Lin et al., Syntex-Synergen Neuroscience Joint Venture), published Apr. 1, 1993, which reports that GDNF is useful for the treatment of nerve injury, including injury associated with Parkinson's disease. Also of interest are a report in Schmidt-Kastner et al., *Mol. Brain Res.*, 26:325–330, 1994 that GDNF mRNA became detectable and was upregulated after pilocarpine-induced seizures; reports in Schaar et al., *Exp. Neurol.*, 124:368–371, 1993 and Schaar et al., *Exp. Neurol.*, 130:387–393, 1994 that basal forebrain astrocytes expressed moderate levels of GDNF mRNA under culture conditions, but that GDNF did not alter basal forebrain ChAT activity; a report in currently pending U.S. application Ser. No. 08/535,682 filed Sep. 28, 1995 that GDNF is useful for treating injury or degeneration of basal forebrain cholinergic neurons; a report in currently pending U.S. application Ser. No. 08/564,844 (by Yan et al.) filed Nov. 29, 1995 that GDNF is useful for treating sensory neuropathy; a report in currently pending U.S. application Ser. No. 08/564,458 (by Yan) filed Nov. 29, 1995 that GDNF is useful for treating retinal ganglion cell injury; and a report in currently pending U.S. application Ser. No. 08/564,833 (by Louis) filed Nov. 29, 1995 that GDNF is useful for treating photoreceptor injury.

Of particular interest are a report in Humpel et al., *Neurosci.*, 59:791–795, 1994 that GDNF mRNA levels in the hippocampus increased after kainic acid-induced seizures and reports in Martin et al., *Brain Res.*, 683:172–178, 1995 and Martin et al., *Soc. Neurosci. Abstr.*, 20:193.12, 1994 that GDNF inhibited seizure activity and seizure-associated neuronal cell loss in the hippocampal, thalamic and amygdaloid regions of the brain that was induced by administration of kainic acid (a non-mammalian excitatory amino acid) (see also currently pending U.S. application Ser. No. 08/340,821 entitled "Methods of Using GDNF as a Neuroprotective Agent" (by Martin) filed Nov. 15, 1994 and U.S. application Ser. No. 07/446,383 filed May 22, 1995. Of additional interest is a report in Perez-Navarro et al., *Eur. J. Neurosci.*, 6:706–711, 1994 that NGF and basic fibroblast growth factor (bFGF) prevented quinolinic acid-mediated decreases in striatal ChAT activity, suggesting that NGF and bFGF may protect striatal cholinergic neurons against quinolinic acid injury. GDNF has not previously been suggested or shown to promote the survival or regeneration of striatal neurons damaged by exposure to quinolinic acid or to exert an effect on neurodegenerative diseases that are associated with NMDA receptor agonist-mediated cell death, such as Huntington's disease There continues to exist a need for methods and therapeutic compositions useful for the treatment of Huntington's disease. Such methods and therapeutic compositions will ideally stop the progression of the degenerative disease and even promote regeneration of the damaged neurons, without severe adverse side effects.

SUMMARY OF THE INVENTION

The present invention provides a method for treating neurodegenerative diseases that are associated with NMDA receptor agonist-mediated cell death by administering a therapeutically effective amount of glial cell line-derived neurotrophic factor (GDNF) protein product. An example of such a neurodegenerative disease is Huntington's disease (HD). It is contemplated that such GDNF protein products would include a GDNF having the amino acid sequence set forth in SEQ ID NO: 1, variants, and derivatives thereof. The invention is based on the discovery that intracerebral administration of recombinant human GDNF attenuated the characteristic cortical and striatal cell death caused by quinolinic acid (QA) administration in an in vivo model of Huntington's disease. GDNF's activity against injury mediated by QA, a specific NMDA receptor agonist, indicates that GDNF will also ameliorate other NMDA receptor-mediated toxicity.

According to the invention, the GDNF protein product may be administered parenterally (preferably intravenously or intracerebroventricularly) at a dose between about 10 μg/kg/day and 100 mg/kg/day, and preferably at a dose between about 1 mg/kg/day and 25 mg/kg/day, and most preferably at a dose between about 5 and 20 mg/kg/day. It is further contemplated that the GDNF protein product be administered with an effective amount of a second therapeutic agent for Huntington's disease.

The invention also provides for the use of GDNF protein product in the manufacture of a medicament for the treatment of Huntington's disease, including reducing neuronal cell death associated therewith.

Numerous additional aspects and advantages of the invention will become apparent to those skilled in the art upon consideration of the following detailed description of the invention which describes presently preferred embodiments thereof.

BRIEF DESCRIPTION OF THE DRAWINGS

FIG. 4 depicts an exemplary GDNF protein product amino acid sequence.

DETAILED DESCRIPTION OF THE INVENTION

Figure 1:
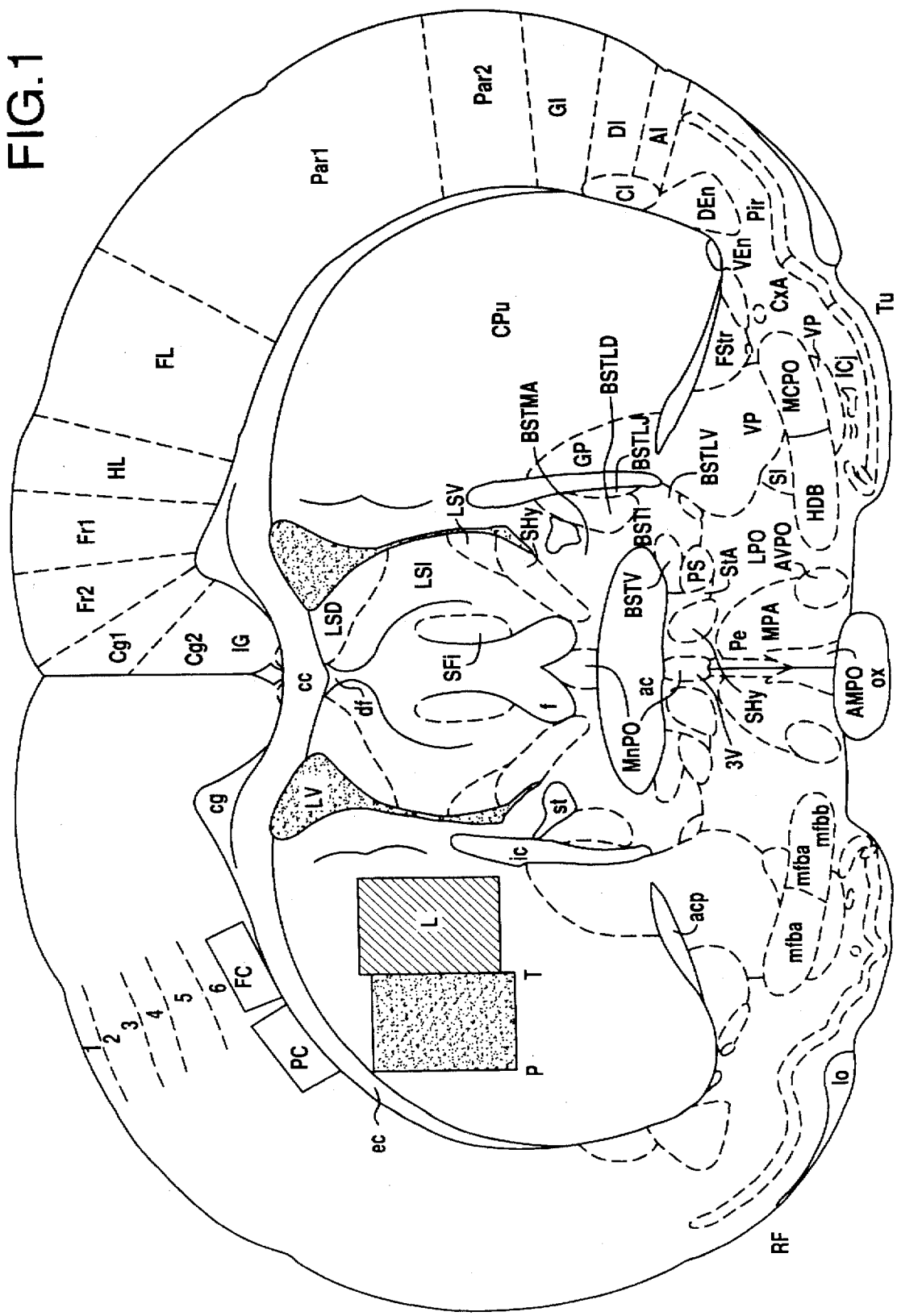
FIG. 1 is a diagram of the cross section of the brain which depicts the areas sampled for viable neuronal cell count and the approximate locations of the striatum, the quinolinic acid-induced lesion site and the transition zone.

The present invention provides a method for reducing neuronal cell death associated with Huntington's disease by administering a therapeutically effective amount of glial cell line-derived neurotrophic factor (GDNF) protein product. The invention may be practiced using any biologically active GDNF protein product, including a GDNF having the amino acid sequence set forth in SEQ ID NO: 1, variants, and derivatives thereof.

The invention is based on the discovery that intracerebral administration of recombinant human GDNF attenuated the characteristic cortical and striatal neuronal cell death caused by quinolinic acid (QA) administration in an art-recognized in vivo model of Huntington's disease. The administration of quinolinic acid is the most commonly used model for studying the progression and potential therapy of Huntington's disease, because it duplicates many of the histopathological features of the disease.

It has been shown that the neuroexcitatory effects of quinolinic acid are mediated by the NMDA-type receptors, because the pattern of evoked discharge mimics that of NMDA, and because competitive NMDA antagonists reduce the quinolinic acid-induced excitation (Martin and Lodge, Neurosci. Lett., 75:175–180, 1987). Thus, GDNF is also expected to ameliorate neuronal injury or degeneration mediated by NMDA receptor agonists. NMDA agonists have been associated with potential involvement in a number of brain disorders, including temporal lobe epilepsy, hepatic encephalopathy, cerebral ischemia, hypoglycemia, and AIDS dementia (Schwarcz and Du, "Quinolinic Acid and Kynurenic Acid in the Mammalian Brain," in Kynurenine and Serotonin Pathways, Schwarcz et al., eds., Plenum Press, NY, 1991).

Different presynaptic and postsynaptic abnormalities affecting glutamate synapses could produce NMDA receptor-mediated neurotoxicity. Presynaptically, there might be excessive neuronal activity, excessive glutamate release, or reduced glutamate uptake (into nerve terminals or glia). Postsynaptically, an abnormally large number of NMDA receptors, altered NMDA receptor-channel complexes (e.g., with increased mean channel open time), reduced average resting potential (leading to decreased $Mg^{2+}$ block), or increased vulnerability to $Ca^{2+}$-mediated damage (e.g., due to reduced $Ca^{2+}$ buffering capability). All could underlie NMDA receptor-mediated injury. In addition, NMDA receptor-mediated toxicity could also be produced by abnormalities in modulatory factors, reduced synaptic $Zn^{2+}$, excess synaptic glycine (Gly), or an abnormal amount of a modifying NMDA agonist (like quinolinate). If NMDA receptor-activated channels are normally partially blocked by an endogenous ligand for the phencyclidine (PCP) site, reduced levels of such a ligand would be another possible source of NMDA receptor-mediated toxicity.

According to the invention, the GDNF protein product may be administered parenterally (including intravenously or intracerebroventricularly) at a dose between about 10 μg/kg/day and 100 mg/kg/day, and preferably at a dose between about 1 mg/kg/day and 25 mg/kg/day, and most preferably at a dose between about 5 and 20 mg/kg/day. It is further contemplated that pharmaceutical compositions which are delivered by methods other than injection are formulated to contain a GDNF protein product dosage sufficient to provide equivalent bioavailability to the parenteral dosage forms. It is further contemplated that the GDNF protein product be administered with an effective amount of a second therapeutic agent for Huntington's disease, such as NGF or bFGF, which have been reported to prevent a quinolinic acid-induced decrease in striatal ChAT activity.

The invention also provides for the use of GDNF protein product in preparation of a medicament for the treatment of Huntington's disease, including reducing neuronal cell death associated therewith.

As used herein, the term "GDNF protein product" includes biologically active purified natural, synthetic or recombinant GDNF and fragments thereof, GDNF variants (including insertion, substitution and deletion variants), and chemically modified derivatives thereof. Also included are biologically active GDNF proteins that are substantially homologous to human GDNF having the amino acid sequence set forth in SEQ ID NO: 1. GDNF protein products may exist as homodimers or heterodimers in their biologically active form.

The term "biologically active" as used herein means that the GDNF protein product demonstrates neurotrophic properties as described in the Examples below, but not necessarily all of the same properties, and not necessarily to the same degree but at least as pertaining to the attenuation of quinolinic acid-induced neuronal cell loss in the cortex and striatum and NMDA receptor agonist-mediated cell death as associated with Huntington's disease and as demonstrated with the GDNF protein product having the amino acid sequence set forth in SEQ ID NO: 1. The selection of the particular neurotrophic properties of interest depends upon the use for which the GDNF protein product is being administered. Using the present description, it is well within the ability of those of ordinary skill in the art to determine whether a given polypeptide has substantially the same biological activity as the GDNF protein products described herein.

The term "substantially homologous" as used herein means having a degree of homology to the GDNF having the amino acid sequence set forth in SEQ ID NO: 1 that is preferably in excess of 70%, more preferably in excess of 80%, and even more preferably in excess of 90% or most preferably in excess of 95%. For example, the degree of homology between the rat and human protein is about 93%, and all mammalian GDNF will have a similarly high degree of homology. The percentage of homology as described herein is calculated as the percentage of amino acid residues found in the smaller of the two sequences which align with identical amino acid residues in the sequence being compared, when an average of three or four gaps in a length of 100 amino acids may be introduced to assist in that alignment, as set forth by Dayhoff, in *Atlas of Protein Sequence and Structure* v. 5, p. 124, National Biochemical Research Foundation, Washington, D.C. (1972), the disclosure of which is hereby incorporated by reference. Thus, the degree of sequence homology may be determined by optimally aligning (with appropriate conservative residue substitutions and disregarding truncations and internal deletions or insertions of the comparison sequence by introducing gaps as required) the amino acid residues of the comparison molecule to those of a GDNF polypeptide, such as depicted in SEQ ID NO: 1, to maximize matches of residues between the two sequences. Once so aligned, the percentage is determined by the number of aligned residues in the comparison polypeptide divided by the total number of residues in the comparison polypeptide, ignoring any additions to the comparison polypeptide which extend beyond the termini of the reference polypeptide. Exemplary conservative substitutions include substitutions within the following groups: glycine, alanine; valine, isoleucine, leucine; aspartic acid, glutamic acid; asparagine, glutamine; serine, threonine; lysine, arginine; and phenylalanine, tyrosine. Also included as substantially homologous is any GDNF protein product which may be isolated by virtue of cross-reactivity with antibodies to the GDNF of SEQ ID NO: 1 or whose genes may be isolated through hybridization with the gene or with segments of the gene encoding the GDNF of SEQ ID NO: 1.

The GDNF protein products according to this invention may be isolated or generated by any means known to those skilled in the art. Exemplary methods for producing GDNF protein products useful in the present invention are described in U.S. patent application Ser. No. 08/182,183 filed May 23, 1994 and its parent applications; PCT Application No. PCT/US92/07888 filed Sep. 17, 1992, published as WO 93/06116 (Lin et al., Syntex-Synergen Neuroscience Joint Venture); European Patent Application No. 92921022.7, published as EP 610 254; and co-owned, co-pending U.S. application Ser. No. 08/535,681 filed Sep. 28, 1995 involving truncated GDNF protein products or GDNF deletion variants, the disclosures of all of which are hereby incorporated by reference.

The full length GDNF polypeptide or fragment can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, NY [1994]). A gene or cDNA encoding the GDNF protein or truncated version thereof may be obtained for example by screening a genomic or cDNA library, or by PCR amplification. Alternatively, a gene encoding the GDNF polypeptide or fragment may be prepared by chemical synthesis using methods well known to the skilled artisan such as those described by Engels et al. (Angew. Chem. Intl. Ed., 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the GDNF polypeptide will be several hundred nucleotides in length. Nucleic acids larger than about 100 nucleotides can be synthesized as several fragments using these methods. The fragments can then be ligated together to form the full length GDNF polypeptide.

In some cases, it may be desirable to prepare nucleic acid and/or amino acid variants of naturally occurring GDNF. Nucleic acid variants (wherein one or more nucleotides are designed to differ from the wild-type or naturally occurring GDNF) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce GDNF. Other preferred variants are those encoding conservative amino acid changes (e.g., wherein the charge or polarity of the naturally occurring amino acid side chain is not altered substantially by substitution with a different amino acid) as compared to wild type, and/or those designed to either generate a novel glycosylation and/or phosphorylation site(s) on GDNF, or those designed to delete an existing glycosylation and/or phosphorylation site(s) on GDNF.

Naturally-occurring GDNF protein products may be isolated from mammalian neuronal cell preparations, or from a mammalian cell line secreting or expressing GDNF. For example, WO93/06116 describes the isolation of GDNF from serum-free growth conditioned medium of B49 glioblastoma cells. GDNF protein products may also be chemically synthesized by any means known to those skilled in the art. GDNF protein products are preferably produced via recombinant techniques because they are capable of achieving comparatively higher amounts of protein at greater purity. Recombinant GDNF protein product forms include glycosylated and non-glycosylated forms of the protein, and protein expressed in bacterial, mammalian or insect cell systems.

In general, recombinant techniques involve isolating the genes responsible for coding GDNF, cloning the gene in suitable vectors and cell types, modifying the gene if necessary to encode a desired variant, and expressing the gene in order to produce the GDNF protein product. Alternatively, a nucleotide sequence encoding the desired GDNF protein product may be chemically synthesized. It is contemplated that GDNF protein product may be expressed using nucleotide sequences which differ in codon usage due to the degeneracies of the genetic code or allelic variations. WO93/06116 describes the isolation and sequencing of a cDNA clone of the rat GDNF gene, and the isolation, sequencing and expression of a genomic DNA clone of the human GDNF gene. WO93/06116 also describes vectors, host cells, and culture growth conditions for the expression of GDNF protein product. Additional vectors suitable for the expression of GDNF protein product in *E. coli* are disclosed in published European Patent Application No. 0 423 980 ("Stem Cell Factor") published Apr. 24, 1991, the disclosure of which is hereby incorporated by reference. The DNA sequence of the gene coding for mature human GDNF and the amino acid sequence of the GDNF is shown in FIG. 19 (SEQ ID NO: 5) of WO93/06116. FIG. 19 does not show the entire coding sequence for the pre-pro portion of GDNF, but the first 50 amino acids of human pre-pro GDNF are shown in FIG. 22 (SEQ ID NO: 8) of WO93/06116.

Naturally-occurring GDNF is a disulfide-bonded dimer in its biologically active form. The material isolated after expression in a bacterial system is essentially biologically inactive, and exists as a monomer. Refolding is necessary to produce the biologically active disulfide-bonded dimer. Processes for the refolding and naturation of the GDNF expressed in bacterial systems are described in WO93/06116. For example, refolding may be accomplished by adding: first dithiothreitol, then glutathione disodium salt, and then a refold buffer to a GDNF-containing extract. Standard in vitro assays for the initial determination of GDNF activity are described in WO93/06116 and in co-owned, co-pending U.S. application Ser. No. 08/535,681 filed Sep. 28, 1995, and hereby incorporated by reference. Such assays include a dopamine uptake assay based on a previously described assay (Friedman et al., *Neuro. Sci. Lett.* 79:65–72, 1987, the disclosure of which is hereby incorporated by reference). Dopamine uptake measures the number and activity of high affinity dopamine reuptake transporter sites and reflects the functional differentiation of dopaminergic neurons.

A. GDNF Variants

The term "GDNF variants" as used herein includes polypeptides in which amino acids have been deleted from ("deletion variants"), inserted into ("addition variants"), or substituted for ("substitution variants"), residues within the amino acid sequence of naturally-occurring GDNF. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made to the amino acid sequence of mature human GDNF provided that the final molecule possesses GDNF biological activity.

Mutagenesis techniques for the replacement, insertion or deletion of one or more selected amino acid residues are well known to one skilled in the art (e.g., U.S. Pat. No. 4,518,584, the disclosure of which is hereby incorporated by reference.) There are two principal variables in the construction of substitution variants: the location of the mutation site and the nature of the mutation. In designing GDNF substitution variants, the selection of the mutation site and nature of the mutation will depend on the GDNF characteristic(s) to be modified. The sites for mutation can be modified individually or in series, e.g., by (1) substituting first with conservative amino acid choices and then with more radical selections depending upon the results achieved, (2) deleting the target amino acid residue, or (3) inserting amino acid residues adjacent to the located site. Conservative changes in from 1 to 20 amino acids are preferred. Once the amino acid sequence of the desired GDNF protein product is determined, a nucleic acid sequence suitable for use in the expression of the protein is readily determined. N-terminal and C-terminal deletion variants may also be generated by proteolytic enzymes.

For GDNF deletion variants, deletions generally range from about 1 to 30 residues, more usually from about 1 to 10 residues, and typically from about 1 to 5 contiguous residues. N-terminal, C-terminal and internal intrasequence deletions are contemplated. Deletions may be introduced into regions of low homology with other TGF-β family members to modify the activity of GDNF. Deletions in areas of substantial homology with other TGF-β family sequences will be more likely to significantly modify GDNF biological activity. The number of consecutive deletions will be selected so as to preserve the tertiary structure of the GDNF protein product in the affected domain, e.g., cysteine crosslinking. Non-limiting examples of deletion variants include truncated GDNF protein products lacking from one to forty N-terminal amino acids of GDNF, or variants lacking the C-terminal residue of GDNF, or combinations thereof, as described in co-owned, co-pending U.S. application Ser. No. 08/535,681 and hereby incorporated by reference.

For GDNF addition variants, amino acid sequence additions typically include N-and/or C-terminal fusions ranging in length from one residue to polypeptides containing a hundred or more residues, as well as internal intrasequence additions of single or multiple amino acid residues. Internal additions may range generally from about 1 to 10 residues, more typically from about 1 to 5 residues, and usually from about 1 to 3 amino acid residues. Examples of N-terminal addition variants include GDNF with an N-terminal methionyl residue (an artifact of the direct expression of GDNF in bacterial recombinant cell culture), which is designated [Met$^{-1}$]GDNF, and fusion of a heterologous N-terminal signal sequence to the N-terminus of GDNF to facilitate the secretion of mature GDNF from recombinant host cells. Such signal sequences generally will be obtained from, and thus be homologous to, the intended host cell species. Additions may also include amino acid sequences derived from the sequence of other neurotrophic factors. A preferred GDNF protein product for use according to the present invention is the recombinant human [Met$^{-1}$]GDNF.

GDNF substitution variants have at least one amino acid residue of the GDNF amino acid sequence removed and a different residue inserted in its place. Such substitution variants include allelic variants, which are characterized by naturally-occurring nucleotide sequence changes in the species population that may or may not result in an amino acid change. Examples of substitution variants (see, e.g., SEQ ID NO: 50) are disclosed in co-owned, co-pending U.S. application Ser. No. 08/535,681 and hereby incorporated by reference.

Specific mutations of the GDNF amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNF amino acid sequence may be modified to add glycosylation sites.

One method for identifying GDNF amino acid residues or regions for mutagenesis is called "alanine scanning mutagenesis" as described by Cunningham and Wells (*Science*, 244:1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions may then be refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNF variants are screened for the optimal combination of desired activity and degree of activity.

The sites of greatest interest for substitutional mutagenesis include sites where the amino acids found in GDNF proteins from various species are substantially different in terms of side-chain bulk, charge, and/or hydrophobicity. Other sites of interest are those in which particular residues of GDNF-like proteins, obtained from various species, are identical. Such positions are generally important for the biological activity of a protein. Initially, these sites are substituted in a relatively conservative manner. Such conservative substitutions are shown in Table 1 under the heading of preferred substitutions. If such substitutions result in a change in biological activity, then more substantial changes (exemplary substitutions) are introduced, and/or other additions or deletions may be made, and the resulting products screened for activity.

TABLE 1

Amino Acid Substitutions

| Original Residue | Preferred Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |

TABLE 1-continued

Amino Acid Substitutions

| Original Residue | Preferred Substitutions | Exemplary Substitutions |
| --- | --- | --- |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce GDNF protein products having functional and chemical characteristics similar to those of natural GDNF. In contrast, substantial modifications in the functional and/or chemical characteristics of GDNF protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for another. Such substituted residues may be introduced into regions of the GDNF protein that are homologous with other TGF-β proteins, or into the non-homologous regions of the molecule.

B. GDNF Derivatives

Chemically modified derivatives of GDNF or GDNF variants may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (e.g., by osmotic pump, or, more preferably, by injection or infusion, or, further formulated for oral, pulmonary or other delivery routes), and determining its effectiveness.

Suitable water soluble polymers include, but are not limited to, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight is between about 2 kDa and about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired; the effects, if any, on biological activity; the ease in handling; the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., *Exp. Hematol.*, 20:1028–1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydrl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed GDNF, or variants thereof, linked to at least one polyethylene glycol molecule, as well as use of GDNF, or variants thereof, attached to one or more polyethylene glycol molecules via an acyl or alkyl linkage.

Pegylation may be carried out by any of the pegylation reactions known in the art. See, for example: *Focus on Growth Factors*, 3(2): 4–10, 1992; EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol (PEG) with the GDNF protein or variant. Any known or subsequently discovered reactive PEG molecule may be used to carry out the pegylation of GDNF protein or variant. A preferred activated PEG ester is PEG esterified to N-hydroxysuccinimide (NHS). As used herein, "acylation" is contemplated to include without limitation the following types of linkages between the therapeutic protein and a water soluble polymer such as PEG: amide, carbamate, urethane, and the like. See *Bioconjugate Chem.*, 5:133–140, 1994. Reaction conditions may be selected from any of those known in the pegylation art or those subsequently developed, but should avoid conditions such as temperature, solvent, and pH that would inactivate the GDNF or variant to be modified.

Pegylation by acylation will generally result in a poly-pegylated GDNF protein or variant. Preferably, the connecting linkage will be an amide. Also preferably, the resulting product will be substantially only (e.g., >95%) mono, di- or tri-pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the GDNF protein or variant in the presence of a reducing agent. Pegylation by alkylation can also result in poly-pegylated GDNF protein or variant. In addition, one can manipulate the reaction conditions to favor pegylation substantially only at the a-amino group of the N-terminus of the GDNF protein or variant (i.e., a mono-pegylated protein). In either case of monopegylation or polypegylation, the PEG groups are preferably attached to the protein via a —CH2—NH— group. With particular reference to the —CH2— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/GDNF protein (or variant) conjugate molecules (meaning GDNF protein or variant to which a polymer molecule has been attached substantially only (i.e., >95%) in a single location). More specifically, if polyethylene glycol is used, the present invention also encompasses use of pegylated GDNF protein or variant lacking possibly antigenic linking groups, and having the polyethylene glycol molecule directly coupled to the GDNF protein or variant.

Thus, GDNF protein products according to the present invention include pegylated GDNF protein or variants, wherein the PEG group(s) is (are) attached via acyl or alkyl groups. As discussed above, such products may be monopegylated or poly-pegylated (e.g., containing 2–6, and preferably 2–5, PEG groups). The PEG groups are generally attached to the protein at the a- or e-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

An exemplary water-soluble polymer for use herein is polyethylene glycol. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable condition used to react a biologically active substance with an activated polymer molecule. Methods for preparing a pegylated GDNF protein product will generally comprise the steps of (a) reacting a GDNF protein product with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/GDNF protein product will generally comprise the steps of: (a) reacting a GDNF protein or variant with a reactive PEG molecule under reductive alkylation conditions, at a pH suitable to permit selective modification of the a-amino group at the amino terminus of said GDNF protein or variant; and (b) obtaining the reaction product(s).

For a substantially homogeneous population of mono-polymer/GDNF protein product, the reductive alkylation reaction conditions are those which permit the selective attachment of the water soluble polymer moiety to the N-terminus of GDNF protein or variant. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any GDNF protein or variant having an a-amino group at the amino terminus, and provide for a substantially homogenous preparation of monopolymer/GDNF protein (or variant) conjugate. The term "monopolymer/GDNF protein (or variant) conjugate" is used here to mean a composition comprised of a single polymer molecule attached to a molecule of GDNF protein or GDNF variant protein. The monopolymer/GDNF protein (or variant) conjugate typically will have a polymer molecule located at the N-terminus, but not on lysine amino side groups. The preparation will generally be greater than 90% monopolymer/GDNF protein (or variant) conjugate, and more usually greater than 95% monopolymer/GDNF protein (or variant) conjugate, with the remainder of observable molecules being unreacted (i.e., protein lacking the polymer moiety). It is also envisioned that the GDNF protein product may involve the preparation of a pegylated molecule wherein the two GDNF monomers are attached by means of a non-peptide polymeric spacer to form the intermolecular linkage of the dimeric molecule. For example, two GDNF molecules may be attached at a non-native or native cysteine residue, such as their respective native $Cys^{101}$ amino acid residues, by means of a PEG moiety as described in WO 92/16221 (International Application No. PCT/US92/02122 by Thompson et al.) the disclosure of which is hereby incorporated by reference.

For the present reductive alkylation, the reducing agent should be stable in aqueous solution and preferably be able to reduce only the Schiff base formed in the initial process of reductive alkylation. Suitable reducing agents may be selected from sodium borohydride, sodium cyanoborohydride, dimethylamine borane, trimethylamine borane and pyridine borane. A particularly suitable reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. GDNF Protein Product Pharmaceutical Compositions

GDNF protein product pharmaceutical compositions typically include a therapeutically or prophylactically effective amount of GDNF protein product in admixture with one or more pharmaceutically and physiologically acceptable formulation materials selected for suitability with the mode of administration. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial CSF, possibly supplemented with other materials common in compositions for parenteral administration. Neutral buffered saline or saline mixed with serum albumin are further exemplary vehicles. The term "pharmaceutically acceptable carrier" or "physiologically acceptable carrier" as used herein refers to a formulation material(s) suitable for accomplishing or enhancing the delivery of the GDNF protein product as a pharmaceutical composition.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the rate of release of GDNF protein product, or for promoting the absorption or penetration of GDNF protein product across the blood-brain barrier.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulation will be determined by one skilled in the art depending upon the route of administration and desired dosage. See for example, *Remington's Pharmaceutical Sciences*, 18th Ed. (1990,Mack Publishing Co., Easton, Pa. 18042) pages 1435–1712, the disclosure of which is hereby incorporated by reference. Such compositions may influence the physical state, stability, rate of in vivo release, and rate of in vivo clearance of the present proteins and derivatives.

Other effective administration forms, such as (1) slow-release formulations, (2) inhalant mists, or (3) orally active formulations are also envisioned. The GDNF protein product pharmaceutical composition may be formulated for parenteral administration. Such parenterally administered therapeutic compositions are typically in the form of a pyrogen-free, parenterally acceptable aqueous solution comprising the GDNF protein product in a pharmaceutically acceptable vehicle. One preferred vehicle is physiological saline. The GDNF protein product pharmaceutical compositions also may include particulate preparations of polymeric compounds such as polylactic acid, polyglycolic acid, etc. or into liposomes. Hyaluronic acid may also be used, and this may have the effect of promoting sustained duration in the circulation.

A particularly suitable vehicle for parenteral injection is sterile distilled water in which the GDNF protein product is formulated as a sterile, isotonic solution, properly preserved. Yet another preparation may involve the formulation of the GDNF protein product with an agent, such as injectable microspheres or liposomes, that provides for the slow or sustained release of the protein which may then be delivered as a depot injection. Other suitable means for the introduction of GDNF protein product include implantable drug delivery devices which contain the GDNF protein product.

The preparations of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol and polyethylene glycol. Suitable complexing agents are for example caffeine, polyvinylpyrrolidone, beta-cyclodextrin or hydroxypropyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as borate, citrate, phosphate, bicarbonate, or Tris-HCl.

The formulation components are present in concentration that are acceptable to the site of administration. For example, buffers are used to maintain the composition at physiological pH or at slightly lower pH, typically within a pH range of from about 5 to about 8.

A pharmaceutical composition may be formulated for inhalation. For example, the GDNF protein product may be formulated as a dry powder for inhalation. GDNF protein product inhalation solutions may also be formulated in a liquefied propellant for aerosol delivery. In yet another formulation, solutions may be nebulized.

It is also contemplated that certain formulations containing GDNF protein product are to be administered orally. GDNF protein product which is administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional excipients may be included to facilitate absorption of GDNF protein product. Diluents, flavorings, low melting point waxes, vegetable oils, lubricants, suspending agents, tablet disintegrating agents, and binders may also be employed.

Another preparation may involve an effective quantity of GDNF protein product in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

D. Administration of GDNF Protein Product

The GDNF protein product may be administered parenterally via a subcutaneous, intramuscular, intravenous, transpulmonary, transdermal, intrathecal or intracerebral route. In addition, protein growth factors that do not readily cross the blood-brain barrier may be given directly intracerebrally or otherwise in association with other elements that will transport them across the barrier. For example, the GDNF protein product may be administered intracerebroventricularly or into the brain or spinal cord subarachnoid space. GDNF protein product may also be administered intracerebrally directly into the brain parenchyma GDNF protein product may be administered extracerebrally in a form that has been modified chemically or packaged so that it passes the blood-brain barrier, or with one or more agents capable of promoting penetration of GDNF protein product across the barrier. For example, a conjugate of NGF and monoclonal anti-transferrin receptor antibodies has been shown to be transported to the brain via binding to transferrin receptors.

To achieve the desired dose of GDNF protein product, repeated daily or less frequent injections may be administered, or GDNF protein product may be infused continuously or periodically from a constant- or programmable-flow implanted pump. Slow-releasing implants containing the neurotrophic factor embedded in a biodegradable polymer matrix can also deliver GDNF protein product. The frequency of dosing will depend on the pharmacokinetic parameters of the GDNF protein product as formulated, and the route of administration.

Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. Appropriate dosages may be ascertained through use of the established assays for determining dosages utilized in conjunction with appropriate dose-response data.

The final dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of GDNF may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein which have the effect of continuous presence in the bloodstream, in predictable amounts, based on a determined dosage regimen. Thus, GDNF protein products include proteins derivatized or otherwise formulated to effectuate such continuous administration. Sustained release forms of the GDNF protein products will be formulated to provide the desired daily or weekly effective dosage.

GDNF protein product cell therapy, e.g., intracerebral implantation of cells producing GDNF protein product, is also contemplated. This embodiment would involve implanting into patients cells capable of synthesizing and secreting a biologically active form of GDNF protein product. Such GDNF protein product-producing cells may be cells that are natural producers of GDNF protein product (analogous to B49 glioblastoma cells) or may be recombinant cells whose ability to produce GDNF protein product has been augmented by transformation with a gene encoding the desired GDNF protein product. Such transformation may be accomplished by means of a vector suitable for delivering the gene as well as promoting its expression and secretion. In order to minimize a potential immunological reaction in patients being administered GDNF protein product of a foreign species, it is preferred that the natural cells producing GDNF protein product be of human origin and produce human GDNF protein product. Likewise, it is preferred that the recombinant cells producing GDNF protein product be transformed with an expression vector containing a gene encoding a human GDNF protein product. Implanted cells may be encapsulated to avoid infiltration of surrounding tissue. Human or non-human animal cells may be implanted in patients in biocompatible, semipermeable polymeric enclosures or membranes that allow release of GDNF protein product, but that prevent destruction of the cells by the patient's immune system or by other detrimental factors from the surrounding tissue. Alternatively, the patient's own cells, transformed to produce GDNF protein product ex vivo, could be implanted directly into the patient without such encapsulation.

GDNF protein product gene therapy in vivo is also envisioned, by introducing the gene coding for GDNF protein product into targeted cells via local injection of a nucleic acid construct or other appropriate delivery vectors. (Hefti, *J. Neurobiol,*. 25:1418–1435, 1994). For example, a nucleic acid sequence encoding a GDNF protein product may be contained in an adeno-associated virus vector for delivery into the targeted cells. Alternative viral vectors include, but are not limited to, retrovirus, adenovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCP Application WO 91/10470 of Aebischer et al., Winn et al., *Exper. Neurol.*, 113:322–329, 1991, Aebischer et al., *Exper. Neurol.*, 111:269–275, 1991; Tresco et al., *ASAIO*, 38:17–23, 1992, each of which is specifically incorporated herein by reference. Techniques for formulating a variety of other sustained- or controlled-delivery means, such as liposome carriers, bio-erodible particles or beads and depot injections, are also known to those skilled in the art.

It is also envisioned that GDNF protein products may be produced by homologous recombination, or with recombinant production methods utilizing control elements introduced into cells already containing DNA encoding GDNF. For example, homologous recombination methods may be used to modify a cell that contains a normally transcriptionally silent GDNF gene or under expressed gene to produce a cell which expresses GDNF. Homologous recombination is a technique originally developed for targeting genes to induce or correct mutations in transcriptionally active genes (Kucherlapati, *Prog. in Nucl. Acid Res. and Mol. Biol.* 36:301 (1989)). The basic technique was developed as a method for introducing specific mutations into specific regions of the mammalian genome (Thomas et al., *Cell.* 44:419–428, 1986; Thomas and Capecchi, *Cell.* 51:503–512, 1987; Doetschman et al., *Proc. Natl. Acad. Sci.* 85:8583–8587, 1988) or to correct specific mutations within defective genes (Doetschman et al., *Nature.* 330:576–578, 1987). Exemplary homologous recombination techniques are described in U.S. Pat. No. 5,272,071 (EP 91 90 3051, EP Publication No. 505 500; PCT/US90/07642, International Publication No. WO 91/09955) the disclosure of which is hereby incorporated by reference.

Through homologous recombination, the DNA sequence to be inserted into the genome can be directed to a specific region of the gene of interest by attaching it to targeting DNA. The targeting DNA is DNA that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize and therefore recombine with other pieces of endogenous DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transferred DNA is incorporated into the genome.

If the sequence of a particular gene is known, such as the nucleic acid sequence of GDNF, the pre-pro sequence or expression control sequence, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

Attached to these pieces of targeting DNA are regions of DNA which may interact with the expression of a GDNF protein. For example, a promoter/enhancer element, a suppresser, or an exogenous transcription modulatory element is inserted in the genome of the intended host cell in proximity and orientation sufficient to influence the transcription of DNA encoding the desired GDNF protein product. The control element does not encode GDNF, but instead controls a portion of the DNA present in the host cell genome. Thus, the expression of GDNF proteins may be achieved not by transfection of DNA that encodes the GDNF gene itself, but rather by the use of targeting DNA (containing regions of homology with the endogenous gene of interest) coupled with DNA regulatory segments that provide the endogenous gene sequence with recognizable signals for transcription of a GDNF protein.

It should be noted that the GDNF protein product formulations described herein may be used for veterinary as well as human applications and that the term "patient" should not be construed in a limiting manner. In the case of veterinary applications, the dosage ranges should be the same as specified above.

Other aspects and advantages of the present invention will be understood upon consideration of the following illustrative examples. Example 1 addresses the effect of GDNF protein product on the neuronal cell loss resulting from intrastriatal infusion of quinolinic acid.

EXAMPLES

Example 1

GDNF Protein Product Effect on Selective Striatal and Cortical Neuronal Cell Loss In this experiment, adult male F344 rats weighing 200–225 g were anesthetized with 2.5% isoflurane+$O_2$ and positioned in a Kopf stereotaxic frame under continued anesthesia. These animals received a unilateral intracerebroventricular (ICV) injection of either rhGDNF (at a dose of 100 µg/4 µl) or vehicle (4 µl of phosphate-buffered saline) over a five minute period into the right lateral cerebral ventricle using a 26-gauge Hamilton syringe. The Hamilton syringe was left in place for a further five minutes before removal. Injection coordinates relative to bregma were: AP −0.8, ML −1.5, at a depth of 3.5 mm from dura. One hour later, quinolinic acid (at a dose of 120 nmol/4 µl) was given intrastriatally over a five minute period using a 26-gauge Hamilton syringe. The Hamilton syringe was left in place for a further five minutes before removal. Injection coordinates relative to bregma were: AP −0.3, ML −3.0, at a depth of 4.5 mm from dura. The animals had their skin sutured with wound clips and were allowed to recover.

At 14 days after the quinolinic acid administration, the rats were anesthetized with sodium pentobarbitone (55 mg/kg given intraperitoneally), and transcardially perfused with phosphate-buffered formalin solution. The brains were removed and immersion-fixed for at least 24 hours in the same fixative. The brains were then dehydrated, embedded in paraffin, cut coronally in 5 µm-thick sections and Nissl stained. Viable cell counts were performed bilaterally in the striatum (hatched area), parietal cortex (PC) and frontal (PC) cortex. The approximate location of these areas is shown in a diagram of a cross-section of the brain in FIG. 1. Areas that are designated (L) in FIG. 1 are the lesion site, and areas designated (T) in FIG. 1 are the transition zone. Sampling was done according to Roberts, "Excitotoxin-Lesioned Rat Striatum," in Lesions and Transplantation, Conn, ed., *Methods in Neurosci.*, 7:28–38, 1991.

Figure 2A:
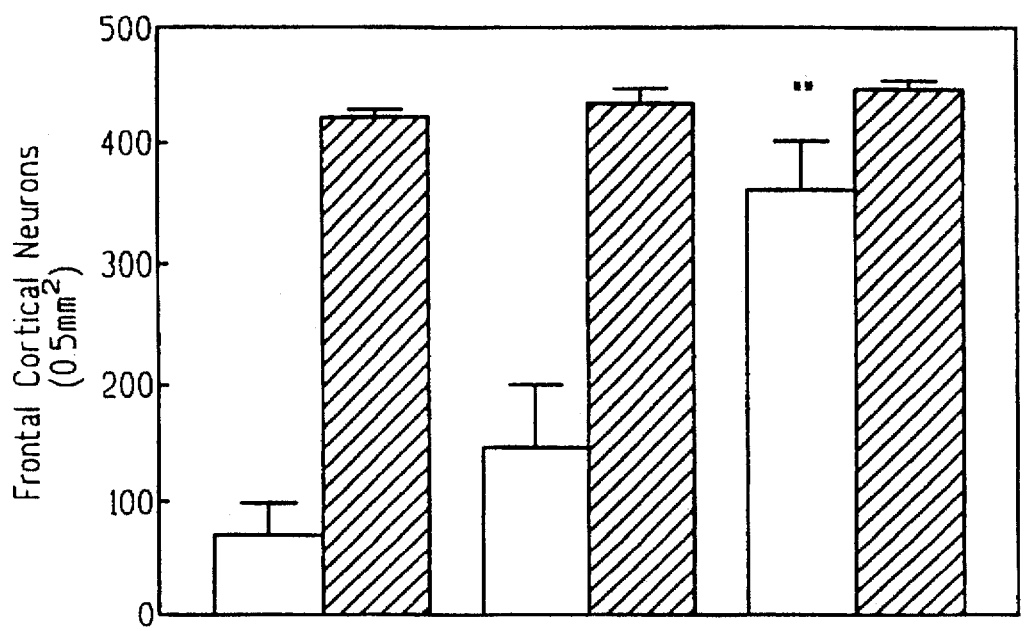
FIGS. 2A and 2B depict the viable neuronal cell counts in the right and left frontal and parietal cortex, respectively, after administration of quinolinic acid (QA), QA and vehicle, or QA and a recombinant human GDNF (e.g., rhGDNF having the amino acid sequence depicted in FIG. 4).
Figure 2B:
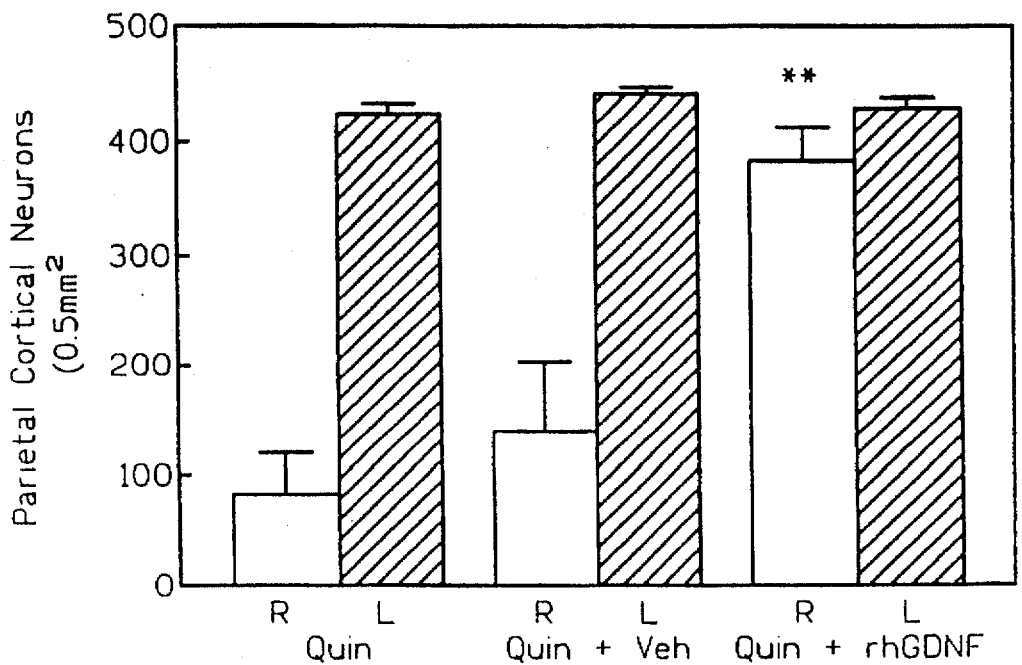

Intrastriatal injection of quinolinic acid consistently produced selective striatal and cortical neuronal cell loss. Viable neuronal cell counts in the frontal and parietal cortex are shown in FIGS. 2A and 2B. Histological examination revealed that ICV rhGDNF significantly ($p<0.01$, student's t-test) attenuated cortical (both parietal and frontal) neuronal cell loss induced by intrastriatal quinolinic acid when compared to vehicle treated animals (see FIGS. 2A and 2B).

Figure 3:
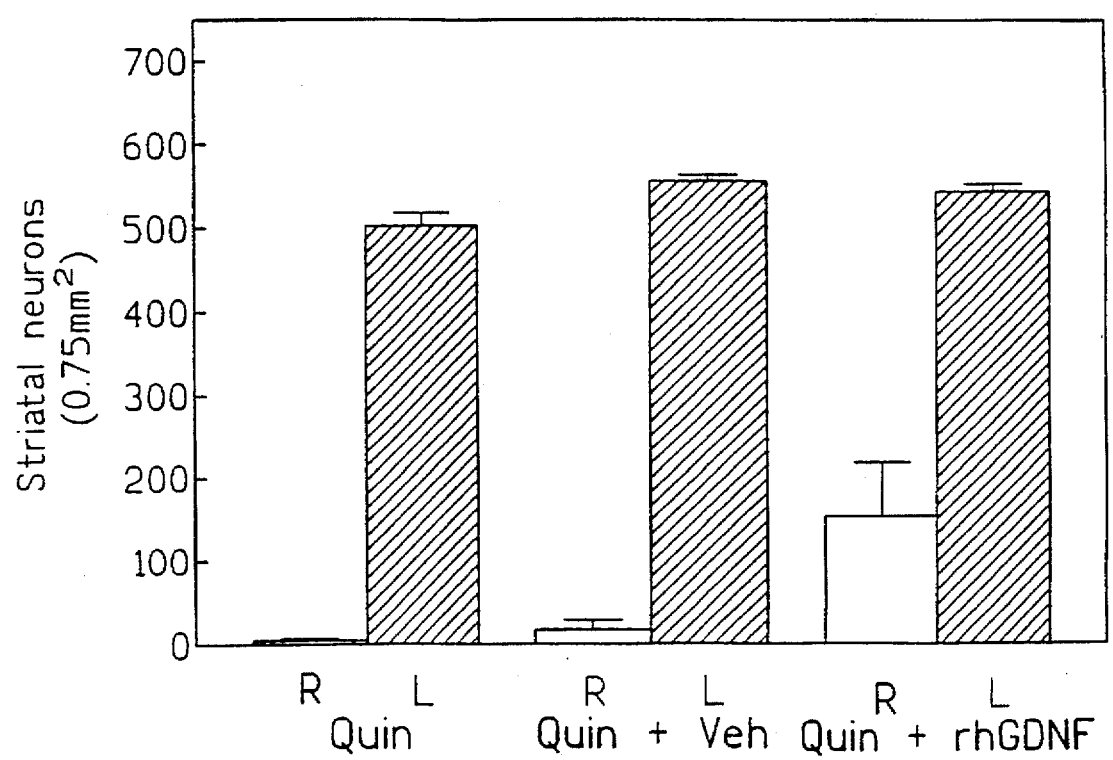
FIG. 3 depicts viable neuronal cell count in the right and left striatum, after administration of QA, QA and vehicle, or QA and rhGDNF.

Viable neuronal cell counts in the striatum are shown in FIG. 3. Quinolinic acid also caused extensive striatal cell loss which was attenuated by the ICV administration of rhGDNF.

These results show that rhGDNF attenuated quinolinic acid-induced neuronal cell loss in the cortex and striatum. This action of rhGDNF extends the therapeutic applications of GDNF protein products to those neurodegenerative diseases that are associated with NMDA receptor agonist-mediated cell death, such as Huntington's disease.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method for treating injury or degeneration of glutamatergic neurons comprising administering to a subject suffering from such disease an effective amount of a glial cell line-derived neurotrophic factor (GDNF) protein product.

2. The method of claim 1, wherein said injury or degeneration is associated with Huntington's disease.

3. The method of claim 1, wherein the GDNF protein product is the amino acid sequence set forth in SEQ ID NO: 1 or a variant, or a derivative thereof.

4. The method of claim 3, wherein the GDNF protein product has the amino acid sequence set forth in SEQ ID NO: 1.

5. The method of claim 3, wherein the GDNF protein product is [Met$^{-1}$]GDNF.

6. The method of claim 3, wherein the derivative comprises a water soluble polymer.

7. The method of claim 6, wherein the water soluble polymer is polyethylene glycol.

8. The method of claim 1, wherein the GDNF protein product is administered at a dose between about 10 µg/kg/day and 100 mg/kg/day.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 134 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ser Pro Asp Lys Gln Met Ala Val Leu Pro Arg Arg Glu Arg Asn Arg
 1               5                  10                  15

Gln Ala Ala Ala Ala Asn Pro Glu Asn Ser Arg Gly Lys Gly Arg Arg
                20                  25                  30

Gly Gln Arg Gly Lys Asn Arg Gly Cys Val Leu Thr Ala Ile His Leu
            35                  40                  45

Asn Val Thr Asp Leu Gly Leu Gly Tyr Glu Thr Lys Glu Glu Leu Ile
        50                  55                  60

Phe Arg Tyr Cys Ser Gly Ser Cys Asp Ala Ala Glu Thr Thr Tyr Asp
 65                 70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
        130
```

9. The method of claim 1, wherein the GDNF protein product is administered at a dose between about 1 mg/kg/day and 25 mg/kg/day.

10. A method of claim 1 wherein said glutamatergic neurons are N-methyl-D-aspartate (NMDA) receptor-type neurons.

11. A method of claim 1 wherein said injury or degeneration is associated with N-methyl-D-aspartate (NMDA) receptor agonist-mediated neuronal cell injury or degeneration.

* * * * *